United States Patent
Earle, Sr. et al.

(10) Patent No.: US 6,486,475 B1
(45) Date of Patent: Nov. 26, 2002

(54) METHOD AND APPARATUS FOR DETERMINING LIQUID ABSORPTION OF AGGREGATE

(75) Inventors: Roger W. Earle, Sr., Dubuque, IA (US); Eric T. Garz, Platteville, WI (US); Peter O. Lee, Dubuque, IA (US); Mark D. Lockwood, Dubuque, IA (US); Jason J. Schmitt, Sherrill, IA (US)

(73) Assignee: Barnstead-Thermolyne Corporation, Dubuque, IA (US)

( * ) Notice: Subject to any disclaimer, the term of this patent is extended or adjusted under 35 U.S.C. 154(b) by 0 days.

(21) Appl. No.: 09/643,329

(22) Filed: Aug. 22, 2000

(51) Int. Cl.[7] .............................................. E01C 19/00
(52) U.S. Cl. .............................. 250/341.8; 250/339.11; 366/16; 366/17; 366/18
(58) Field of Search ..................... 250/339.11, 341.8; 366/16, 17, 18

(56) References Cited

U.S. PATENT DOCUMENTS

| | | | |
|---|---|---|---|
| 4,266,878 A | 5/1981 | Auer | |
| 4,871,917 A | 10/1989 | O'Farrell et al. | |
| 5,017,787 A | 5/1991 | Sato et al. | |
| 5,087,817 A | 2/1992 | Chiba et al. | |
| 5,590,976 A | 1/1997 | Kilheffer et al. | |
| 5,605,841 A | * 2/1997 | Johnsen | 250/339.11 |
| 5,755,041 A | 5/1998 | Horwitz | |
| 5,801,337 A | 9/1998 | Peake | |
| 5,870,926 A | 2/1999 | Saito et al. | |
| 5,908,240 A | * 6/1999 | Hood | 366/18 |

* cited by examiner

Primary Examiner—Constantine Hannaher
Assistant Examiner—Andrew Israel
(74) Attorney, Agent, or Firm—Wood, Herron & Evans, L.L.P.

(57) ABSTRACT

A method of determining liquid absorption of an aggregate comprises providing a sample of the aggregate, adding liquid to the sample, subjecting the sample to a light source signal, monitoring a light reflected signal reflected from the sample and controlling addition of liquid to the sample as a function of the light reflected signal. The apparatus comprises a support for supporting a sample of the aggregate, a liquid source for adding liquid to the sample, a light source which subjects the sample to a light source signal, a light sensor which senses a reflected light signal reflected from the sample and a processor/controller which controls addition of liquid from the liquid source as a function of the reflected light signal. The light source is preferably an infrared source and the light sensor is preferably an infrared detector. The sample is weighed in a dry state and in the saturated surface dry ("SSD") state and the percent by weight of aggregate water absorption and hence aggregate binder absorption and/or bulk specific gravity is then calculated. A weighing device can be incorporated directly into the apparatus.

65 Claims, 4 Drawing Sheets

METHOD AND APPARATUS FOR DETERMINING LIQUID ABSORPTION OF AGGREGATE

FIELD OF THE INVENTION

This invention relates generally to paving material, and more particularly to a method and apparatus for determining liquid absorption of aggregate. Specifically this invention is for determining the saturated, surface-dry state of aggregate and for determining the amount of water and hence binder absorbed by an aggregate in order to determine the proper amount of binder to be added to a given amount of aggregate to produce paving material of acceptable mechanical qualities.

BACKGROUND OF THE INVENTION

To design an asphalt paving mix, the proper amount of asphalt binder must be added to a given amount of aggregate material to maintain the right matrix of aggregate and binder in order to produce a paving material which will yield a strong and durable road. If there is too much binder in the mix, the road will be soft and rutting will occur. If there is not enough binder in the mix, the road will be brittle and will crumble or break apart.

Aggregates used in the preparation of asphalt for road construction are tested to determine the amount of asphalt binder that will be absorbed internally into the aggregate when a batch is prepared. When binder is absorbed internally into the porous aggregate, that absorbed binder does not contribute to the effective volume of the asphalt mix. In order to account for this, additional binder must be added, which essentially disappears in the mix. The measurement of the binder absorbed by the aggregate which does not contribute to the volume of the asphalt mix is the percent absorption, by weight, of water absorbed into the aggregate to the weight of the aggregate itself ("PA").

The procedure for testing aggregate for PA is as follows. A sample of the dry aggregate is prepared to a condition where the internal voids are saturated with water, and the surface of the aggregate is dry. This condition is known as the saturated surface dry ("SSD") state. The SSD sample is then weighed. The sample is then dried completely in an oven, and weighed again (dry). The difference between the SSD and dry weights, divided by the dry weight, and multiplied by 100, yields the PA.

Another useful measurement is bulk specific gravity ("BSG"). BSG is defined as the mass of the material dry divided by the volume of the material at SSD. To determine the volume of the material at SSD the material in the SSD state is immersed in water and the volume of water displaced is equal to the volume of the material at SSD.

One method for preparing a sample of aggregate to the SSD condition is what is know as the "towel dry" method. In this method totally saturated aggregate, i.e. aggregate wetter than SSD, is patted with a paper towel just to the point where the aggregate surface is dry. This technique is best used for larger aggregate such as that for concrete.

The current preferable method for determining whether aggregate for asphalt or concrete is at SSD is what is known as the "slump" test. In this test, a sample of aggregate is prepared with excess water so that it is wetter than the SSD state. The aggregate is placed into a metal cone, the metal cone is placed atop a non-absorbent surface of a table or bench and the aggregate is tamped down into the cone, through an opening in the tip of the cone, with a metal tamper. With aggregate pieces having water on the surface, i.e. with the aggregate sample being wetter than the SSD state, the cone of aggregate will remain standing when the metal cone is removed. The water between the particles of aggregate holds the aggregate together, due to surface tension. The SSD point is reached when there is a "slight slump" of the aggregate when the metal cone is removed. Once the aggregate sample has been initially prepared to wetter than the SSD state the aggregate is progressively agitated and subjected to warm air flowing over it, repacked into the metal cone and the metal cone removed, until this slight slump occurs. A 500 gram sample is then taken from the SSD aggregate and weighed. The 500 gram sample is then completely dried in an oven and is weighed again. The PA is then computed from the two weights.

There are a number of problems with the slump test. First, the test is subjective. The definition of a "slight slump" will vary from technician testing the aggregate to the next. In addition, while the slump test works fairly well with natural sand, for which the test was originally developed, the test does not work as well for jagged material such as crushed granite and limestone. The crushed materials have a higher angularity (jaggedness) and a higher content of fine material, which packs better in the cone, holding the packed material together better. This requires the material to dry more before exhibiting a "slight slump", making for an artificially dryer SSD point. On the other hand, a method which could actually measure the presence or absence of water on the surface of the aggregate would give a much more accurate measurement of whether the aggregate was in the SSD state or not and hence produce a much more accurate PA measurement.

Second, when the sample is at a temperature above room ambient, it will continue to lose water weight by evaporation as long as the sample remains on the table or bench. This produces an artificially low PA. Also, the time between reaching SSD and weighing the sample will not be consistent from batch to batch and technician to technician. If the sample could maintain its SSD condition/moisture content from the time that that condition is reached until the sample is weighed then the measurement would be more accurate and repeatable from batch to batch and technician to technician.

Third, as the sample is agitated and dried, the sample will begin to generate dust, which leaves the sample, and thus alters the aggregate constitution. Dust can also adversely effect mechanical parts such as bearings, motors, couplings etc. of the equipment used in the SSD/PA testing, thus contributing to premature failure of same. The dust is also a nuisance to the technicians operating the equipment. It would be desirable to somehow contain the dust generated by the sample during the SSD/PA determination.

SUMMARY OF THE INVENTION

The present invention solves the noted problems of the slump test in connection with determining BSG and PA, while providing for the liquid absorbing characteristics of aggregate to be determined. The invention is both method and apparatus for determining liquid absorption of aggregate, for determining the SSD state of an aggregate, and for determining the PA of an aggregate.

The method of determining liquid absorption of an aggregate comprises providing a sample of the aggregate, adding liquid to the sample, subjecting the sample to an infrared light source signal and monitoring an infrared light reflected signal reflected from the sample.

Another method of determining liquid absorption of an aggregate comprises providing a sample of the aggregate, adding liquid to the sample, subjecting the sample to a light source signal, monitoring a light reflected signal reflected from the sample and controlling either addition of liquid to the sample or removal of liquid from the sample as a function of the light reflected signal. Preferably the controlling step is controlling addition of liquid to the sample.

The liquid is preferably water. The light source signal is preferably an infrared source signal and the light reflected signal is preferably an infrared reflected signal.

The method further comprises agitating the sample. One manner of agitation comprises moving the sample in an orbital motion. Another manner of agitation comprises moving the sample in a wobbling motion. A third manner of agitation comprises stirring the sample. Preferably the agitating step comprises a combination of the three, namely moving the sample in an orbital motion, moving the sample in a wobbling motion and stirring the sample.

Preferably liquid is added to the sample only until the reflected light signal reaches a predetermined value indicative of the sample being at the SSD state. The predetermined value of the reflected light signal is determined by averaging the reflected light signal reflected from the dry sample with the reflected light signal reflected from the sample when wetter than the SSD state. The reflected light signal reflected from the dry sample, which can vary from aggregate to aggregate, is measured with the apparatus of the present invention and the value of the reflected light signal reflected from the sample wetter than SSD is a constant for all aggregate.

Weighing the sample in the dry state and in the SSD state enables the technician to additionally determine the PA of the aggregate.

The method may alternatively comprise heating the sample to remove liquid from the sample, with the controlling step controlling removal of liquid from the sample as a function of the reflected light signal by controlling the heating of the sample.

The apparatus of the present invention comprises a support for supporting a sample of the aggregate, a liquid source for adding liquid to the sample, an infrared light source which subjects the sample to an infrared light source signal and an infrared light sensor which senses a reflected infrared light signal reflected from the sample.

The apparatus of the present invention also comprises a support for supporting a sample of the aggregate, a liquid source for adding liquid to the sample, a light source which subjects the sample to a light source signal, a light sensor which senses a reflected light signal reflected from the sample and a processor/controller which controls either addition of liquid from the liquid source to the sample or removal of liquid from the sample as a function of the reflected light signal. Preferably the processor/controller controls addition of liquid from the liquid source to the sample.

The liquid source is preferably a water source, the light source is preferably an infrared source and the light sensor is preferably an infrared detector.

The apparatus further preferably includes an agitator for agitating the sample. The agitator may be a turntable which moves the sample in an orbital motion, a turntable which moves the sample in a wobbling motion or a stirrer which stirs the sample. Preferably the agitator is a combination of all three, namely a turntable which moves the sample in an orbital motion and in a wobbling motion and a stirrer which stirs the sample.

The support is preferably a bowl which contains the sample. The bowl preferably includes an island in the center thereof to direct the sample radially outwardly. The bowl preferably includes a lid thereon. The lid preferably includes a dome offset from the center of the lid. The light source and light sensor are preferably positioned such that the light source signal and light reflected signal pass through the dome normal to a surface of the dome. The light source is preferably an infrared source and the light sensor is preferably an infrared detector. The apparatus preferably includes a cabinet containing the support, the liquid source, the light source and the light sensor. The cabinet preferably includes a door providing access to an interior thereof. A bracket is preferably mounted to an underside of the door, and the light source and light sensor are preferably mounted to this bracket.

The processor/controller preferably processes the reflected light signal as a function of time and controls addition of liquid to the sample such that liquid is added to the sample only until the reflected light signal reaches a predetermined value indicative of the sample being at the SSD state. The reflected light signal reflected from the dry sample, which can vary from aggregate to aggregate, is measured with the apparatus of the present invention and the value of the reflected light signal reflected from the sample wetter than SSD is a constant voltage for all aggregate.

The apparatus may alternatively include a weight indicating device for weighing the sample in the dry state and in the SSD state to thereby additionally determine the PA of the aggregate.

The apparatus may further include a heater for removing liquid from the sample, in which case the processor/controller controls removal of liquid from the sample as a function of the reflected light signal by controlling the heater.

The present invention thus avoids the subjectivity of the slump test, replacing it with a much more scientific empirical test which actually measures the presence or absence of water on the surface of the aggregate. The present invention also avoids the problem of the slump test wherein continual water evaporation, after reaching SSD, produces an artificially low PA, since the moistened aggregate is maintained in a bowl sealed with a lid thereby preventing moisture escape. Further, the bowl with lid sealed thereon eliminates the generation of dust as the initially dry sample is begun to be agitated during initial addition of water to the sample.

These and other advantages of the present invention will become more readily apparent during the following detailed description taken in conjunction with the drawings herein, in which:

BRIEF DESCRIPTION OF THE DRAWINGS OF THE INVENTION

DETAILED DESCRIPTION OF THE INVENTION

Figure 1:
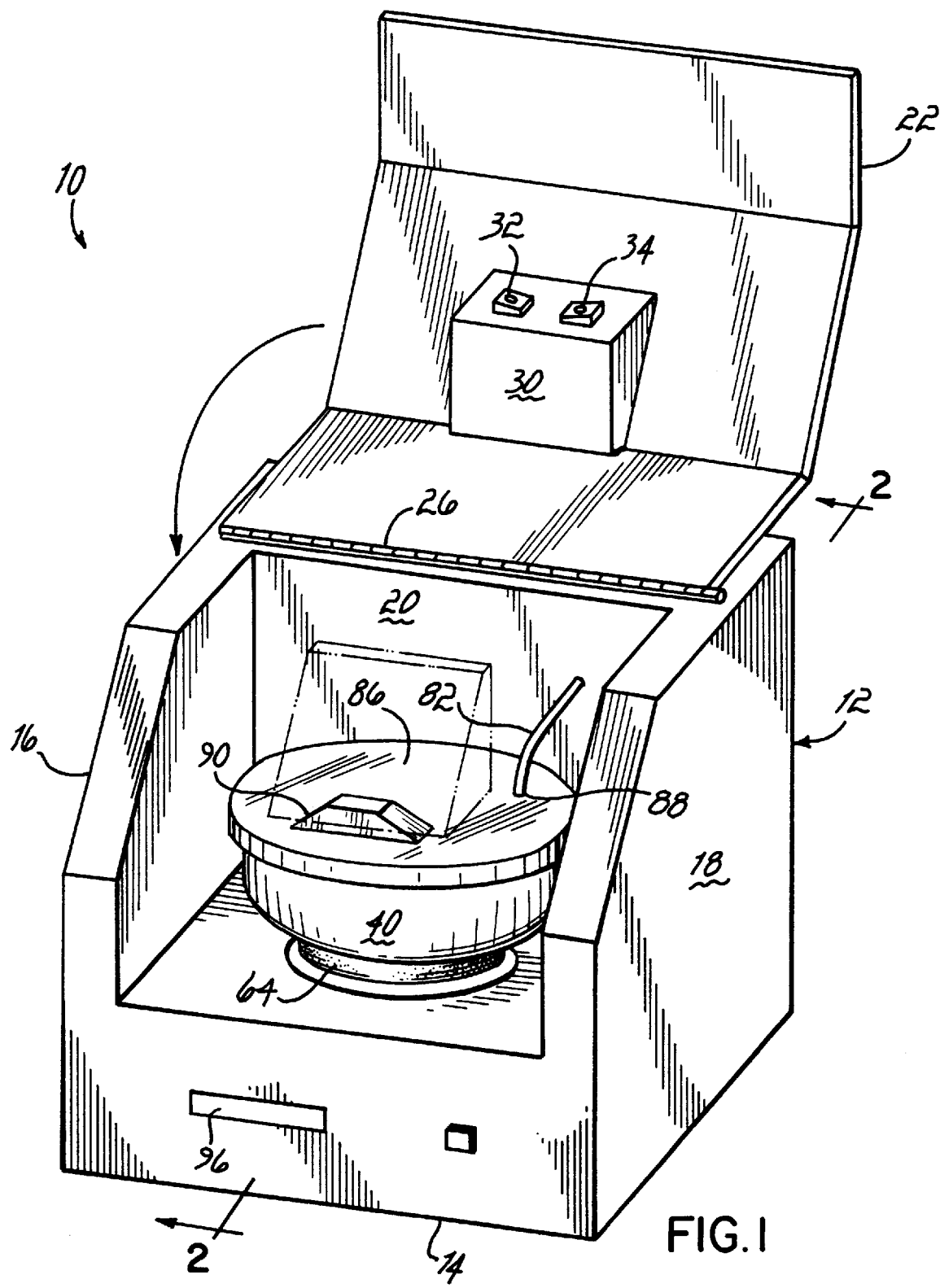
FIG. 1 is a perspective view of the apparatus of the present invention.

Referring first to FIG. 1, there is illustrated apparatus 10 embodying the principles of the present invention for determining liquid absorption of aggregate, for determining the SSD state of an aggregate and for determining the PA of an aggregate.

The apparatus 10 comprises a cabinet 12 having a base 14, a pair of opposed side walls 16, 18 and a back wall 20. An openable and closeable door 22 is pivoted to a partial top wall 24 via hinge 26 and forms the remainder of the top and front of the cabinet 12. Mounted to the underneath side of the door 22 is a bracket 30 to which are mounted an infrared source 32 and an infrared detector 34, the operation of which will be described below.

Figure 2:
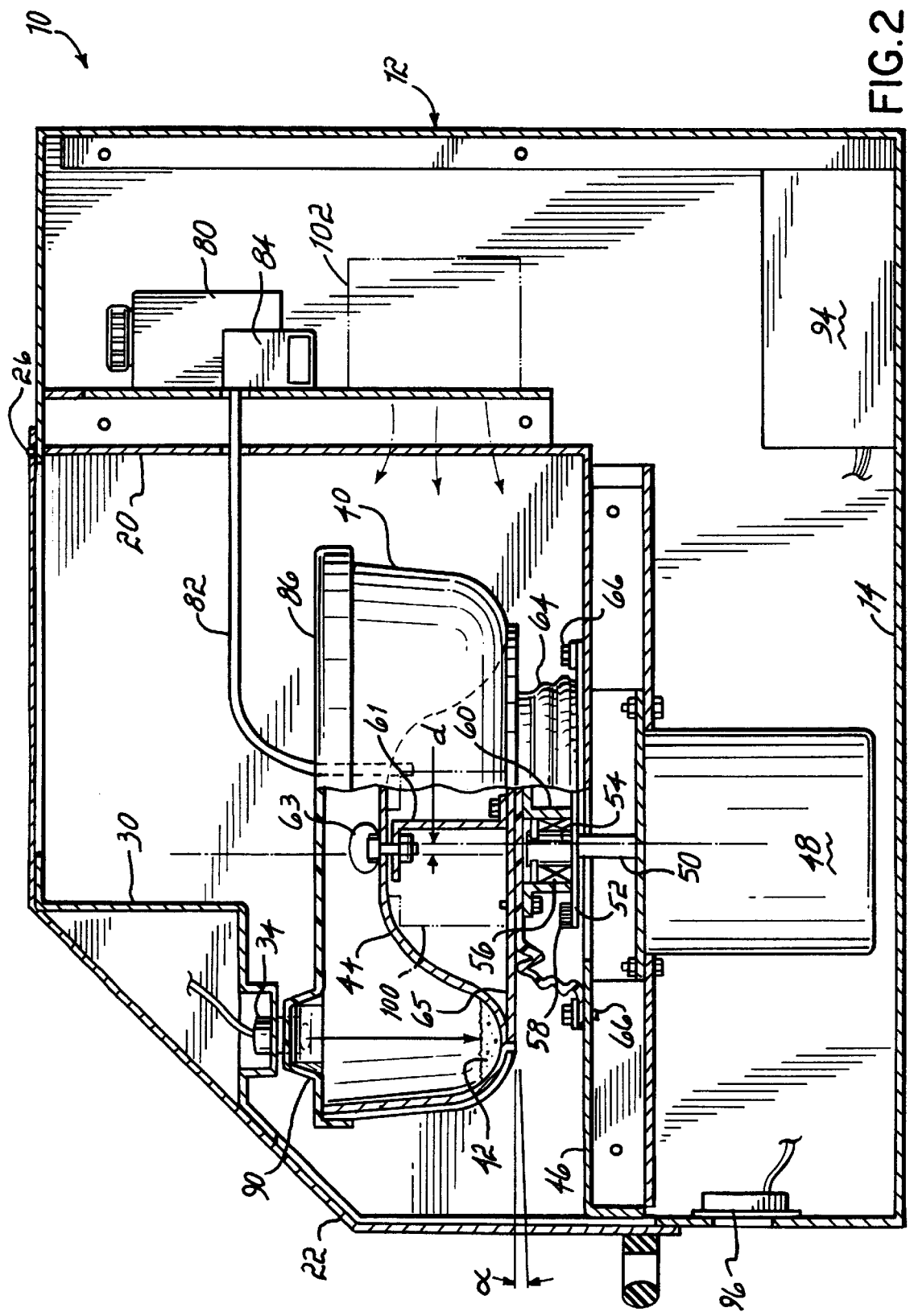
FIG. 2 is a view taken along line 2—2 of FIG. 1.
Figure 3:
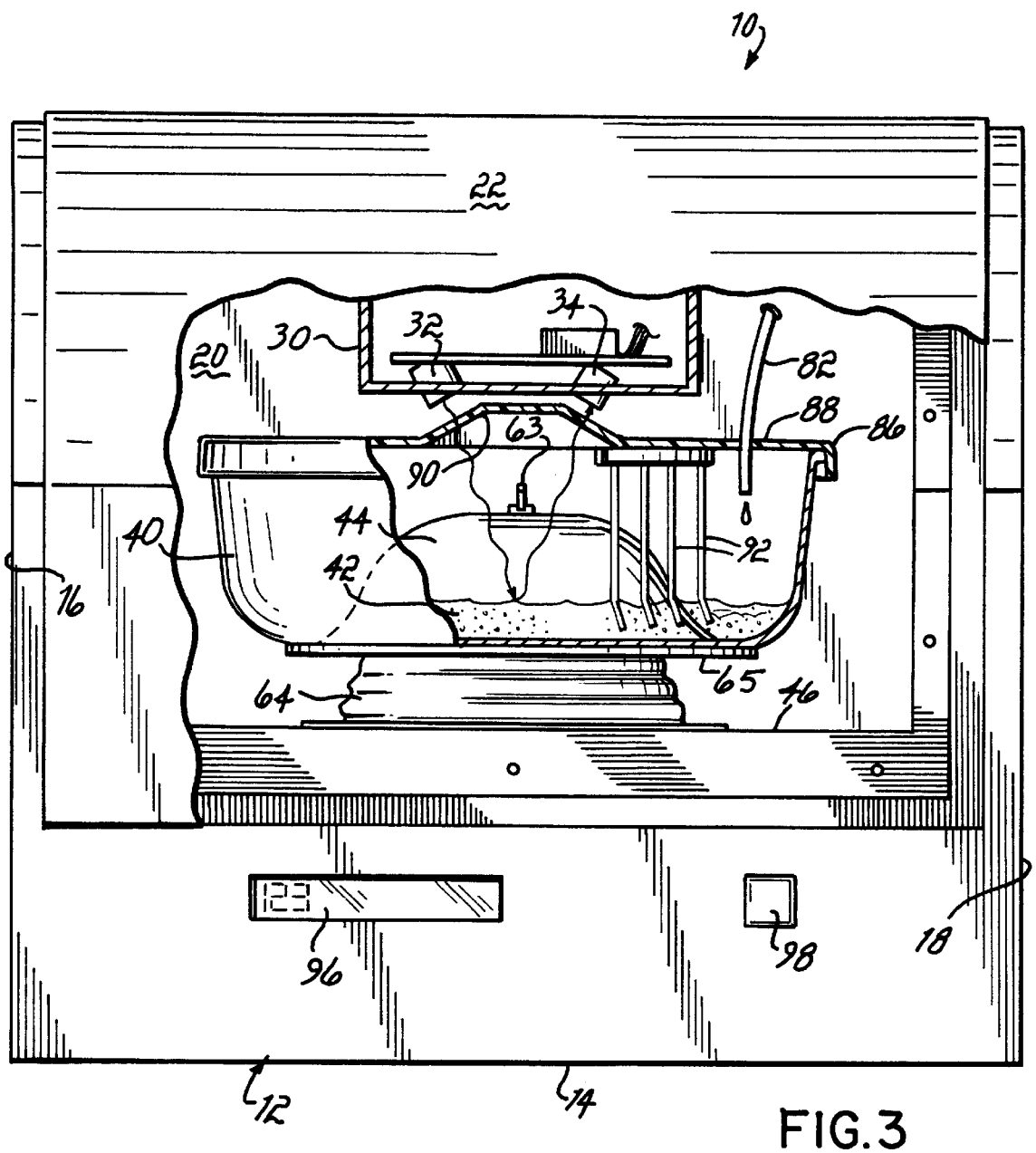
FIG. 3 is a front view of the apparatus, partially broken away.

Referring now to FIGS. 2 and 3, the apparatus 10 is shown in more detail. A support in the form of a bowl 40 is provided for containing a sample 42 of aggregate. The bowl 40 includes an island 44 in the center thereof to direct the aggregate 42 radially outwardly during motion of the bowl 40, which will be described below. A horizontal wall 46 interconnects the front, side and back walls 14, 16, 18 and 20 and provides structure upon which the bowl 40 is mounted.

A motor 48 is mounted to the horizontal wall 46 and includes an output drive shaft 50. Output drive shaft 50 has fixedly secured thereto a plate 52 and an eccentric shaft 54. The axes of rotation of the shafts 50, 54 are angled just off of parallel by approximately 0.75°. The axis of rotation of the shaft 54 is offset from that of shaft 50 a distance d. Preferably, d is approximately 0.078" on average. A bearing 56 encircles eccentric shaft 54. The inner race of the bearing 56 is fixedly secured to the eccentric shaft 54. A counterweight 58 is mounted to the plate 52 to offset or counterbalance the effects of the shaft 54 being offset from the shaft 50 the amount d. The outer race of the bearing 56 is fixedly secured to an inverted flanged cylinder 60. A Z bracket mounts stop a plate 65. A ¼ turn thumb nut 63 removably secures the bowl 40 onto the top of the Z bracket. A rubber boot 64 has an upper end sandwiched between the flanged cylinders 60 and plate 61, and a lower end secured to the horizontal wall 46 via screws 66 or the like. Screws 62 pass through plate Z bracket 61, plate 65, boot 64 and screw into cylinder 60. Boot 64 protects bearing 56, etc. from contamination and also serves to prevent bowl 40 from rotating about its own axis.

Due to the offset d, rotation of motor output shaft 50 causes bowl 40 to move in an "orbital" motion having a radius equal to d. The 0.75° deviation from parallel between the axes of shafts 50, 54 imparts a "wobbling" motion to the bowl 40 and hence sample of aggregate 42.

Referring now to FIGS. 1–3, a water reservoir 80 is mounted to rear wall 20 and includes flexible tubing or a hose 82 connected thereto. Hose 82 preferably has a 0.01 inch diameter nozzle or output end. A pump 84 pumps water from reservoir 80 through hose 82 into bowl 40 at a preferred rate of approximately 8 micro liters per second. A removable lid 86 seals the sample 42 within the bowl 40, and includes a small hole 88 through which the tube 82 passes. The lid 86 includes a domed region 90. The domed region 90 allows signals from the infrared source 32 and to the infrared detector 34 to pass through the lid 86 normal thereto. Domed region 90 preferably includes a pair of angled surfaces 90a and 90b which allow signals from the infrared source 32 and to the infrared detector 34 to pass therethrough normal thereto. Wire fingers 92 are mounted within the bowl 40 and extend downwardly into contact with the sample 42 of aggregate and serve to further break apart particles of the sample 42 by stirring during injection of water into bowl 40. A processor/controller 94 is operably connected to the infrared source 32, infrared detector 34 and to a display panel 96 on front wall 14 of cabinet 12. An on/off switch 98 is also mounted on front wall 14 of cabinet 12.

Figure 4:
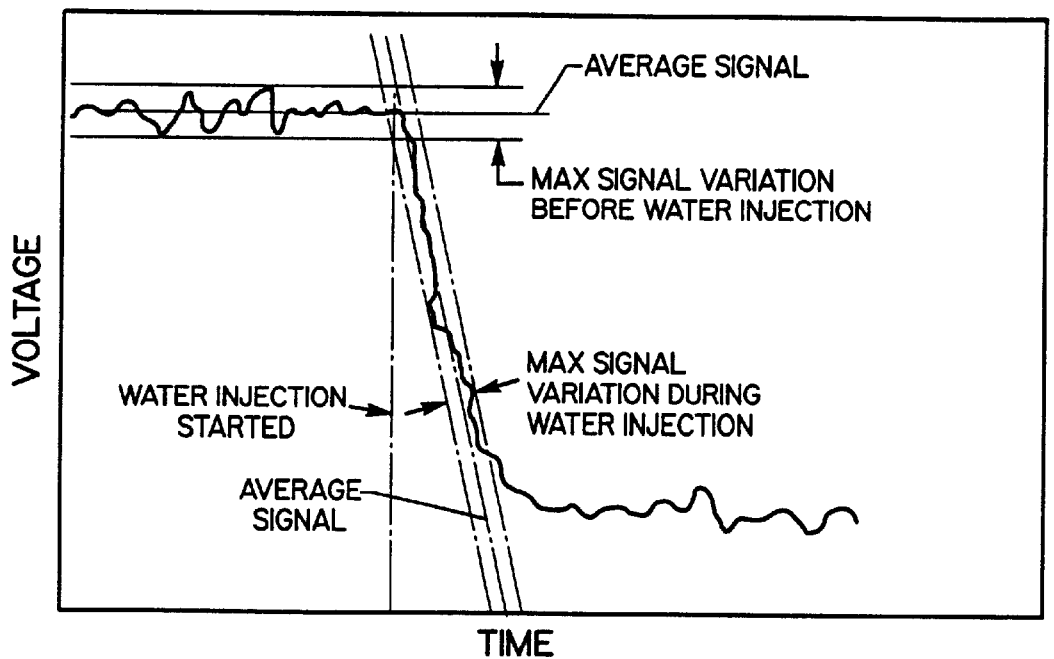
FIG. 4 is a plot of actual voltage of the infrared detector as a function of time as the sample goes from a dry state to an SSD state and beyond to wetter than SSD.
Figure 5:
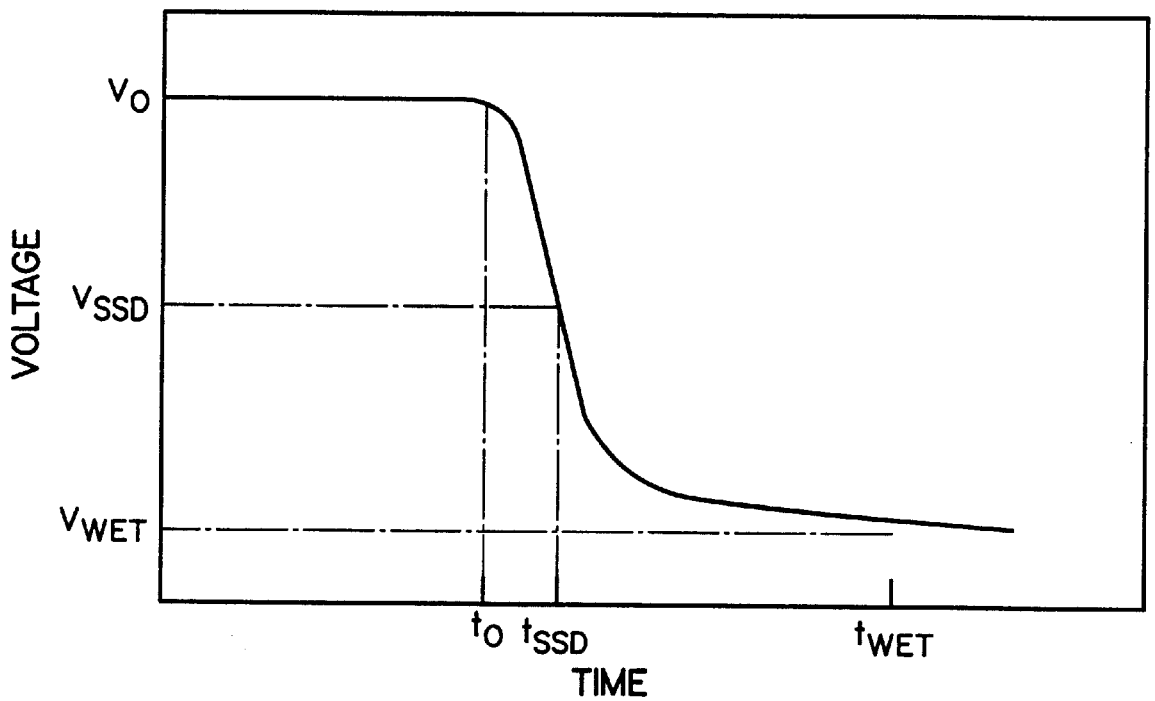
FIG. 5 is an average of the voltage plot of FIG. 4 illustrating the SSD point.

Referring now to FIGS. 4 and 5, the processor/controller 94 preferably processes the reflected infrared signal reflected from the moistened aggregate 42 as a function of time, and controls addition of water to the sample 42 via the pump 84 such that liquid is added to the sample 42 only until the reflected light signal reaches a predetermined value indicative of the sample being at the SSD state, which will be described in more detail below. As is illustrated in FIG. 4, the actual or "raw" infrared reflected voltage indicated by infrared detector 34 as a function of time decreases during addition of water to the sample 42 and during mixing or agitation of the sample 42 therewith. The infrared source 32 and infrared detector 34 are mounted in an isosceles triangle configuration, wherein the IR source and detector define two points and the surface to be measured, i.e. the surface of the aggregate sample 42, defines the third point. Light travels from the infrared source 32 to the aggregate 42, scatters back off the aggregate 42, and then travels to the infrared detector 34. Because water is very optically absorbing at wave lengths above 1.8 micrometers, and particularly in the range of 2.5–3.5 micrometers, the signal of the infrared detector 34 will decrease as the voids in the aggregate fill with water. The signal will show a saturating effect when the voids become completely filled with water. At the point where the aggregate 42 becomes wetter than SSD, the slope of the curve shown in FIG. 4 asymptotically approaches zero. The SSD point occurs at a point in time prior thereto, as will be described below in more detail. The processor/controller 94 monitors the infrared reflected signal via an analog to digital converter (not shown). To isolate the reflected infrared signal from any thermal effect noise of the thermopile infrared detector 34, the infrared source 32 is modulated at approximately one Hz. The electrical circuit (not shown) associated with the IR source 32 and detector 34 preferably includes an electronic high pass filter and a signal rectifier to provide a dc output signal for the processor/controller 94.

Referring now specifically to FIG. 5, FIG. 5 illustrates the average of the voltage signal versus time curve of FIG. 4 as averaged by the processor/controller 94. The voltage signal $V_0$ at time $t_0$ is the voltage representative of the IR reflectance of the dry aggregate. The voltage signal $V_{wet}$ at time $t_{wet}$ is the voltage representative of the IR reflectance of the aggregate wetter than SSD. It has been empirically determined that the voltage signal $V_{ssd}$ at time $t_{ssd}$ is approximately equal to the average of $V_0$ and $V_{wet}$. In other words, it has been empirically determined that $V_{ssd}$ is approximately equal to $(V_0+V_{wet})/2$. It has also been determined empirically that $V_{wet}$ for most aggregates is approximately a constant voltage. Thus, once $V_0$ has been measured for a particular aggregate, $V_{ssd}$ can be readily calculated with the above formula and the processor/controller can then be programmed with the calculated $V_{ssd}$ value. The processor/controller monitors the voltage and controls addition of water to the sample 42 such that water is added only until the voltage reaches the predetermined $V_{ssd}$ value.

To automatically determine the PA of an aggregate, the apparatus 10 could advantageously incorporate a weighing scale 100 to record the weight of the sample 42 dry and at the SSD point, in real time.

To determine the SSD state of an aggregate going from wet to dry, the apparatus would include a heater 102 controlled by the processor/controller 94 to perform the reverse of the above, i.e. to remove liquid from the sample 42 by heating it.

Cabinet 12 may be fabricated of aluminum sheet. A suitable material from which to fabricate the bowl 40 and lid 86 is polyethylene. The thickness of the polypropylene in the area of the domed region 90 is preferably 0.02 inches or less. A suitable infrared source or emitter 32 is ReflectIR available from Ion Optics of Waltham, Mass. A suitable infrared detector or receiver 34 is DZMHS005 available from Dexter Research of Dexter, Mich. A suitable motor 48 is Type 04 available from Fasco Motors of Ozark, Mo. A suitable pump 84 is 090SP-24-8 available from Bio-Chem Valve, Inc. of Benton, N.J.

Those skilled in the art will readily recognize numerous adaptations and modifications which can be made to the present invention which will result in an improved method and apparatus for determining liquid absorption of aggregate, yet all of which will fall within the spirit and scope of the present invention as defined in the following claims. For example, while the invention has been described in connection with determining the SSD state of an aggregate in going from a dry condition of the aggregate to a wet condition, the invention can also be practiced in the reverse, i.e. going from an overly saturated condition of the aggregate to a SSD condition of the aggregate. However, the SSD state of the aggregate, as determined by infrared reflection, is more readily obtained for the dry to wet process than for the wet to dry process. Additionally, the wet to dry process requires a heating means be incorporated into the apparatus. The infrared source or emitter could be an IR LED as opposed to an IR lamp, and the IR thermopile detector could be an IR photo diode. Other forms of agitation such as low frequency vertical vibration or ultrasonic could be employed. The domed region comprising angled surfaces 90a and 90b could be fabricated from sapphire. Accordingly, the invention is to be limited only by the scope of the following claims and their equivalents.

What is claimed is:

1. A method of determining liquid absorption of an aggregate, the method comprising:
   providing a sample of the aggregate;
   adding liquid to the sample;
   subjecting the sample to a light source signal;
   monitoring a light reflected signal reflected from the sample; and
   controlling one of addition of liquid to the sample and removal of liquid from the sample as a function of the light reflected signal.

2. The method of claim 1 wherein the controlling step comprises controlling addition of liquid to the sample.

3. The method of claim 2 wherein the liquid is water.

4. The method of claim 2 wherein the light source signal is an infrared source signal and the light reflected signal is an infrared reflected signal.

5. The method of claim 2 further comprising agitating the sample.

6. The method of claim 5 wherein the agitating step comprises moving the sample in an orbital motion.

7. The method of claim 5 wherein the agitating step comprises moving the sample in a wobbling motion.

8. The method of claim 5 wherein the agitating step comprises stirring the sample.

9. The method of claim 5 wherein the agitating step comprises moving the sample in an orbital motion, moving the sample in a wobbling motion and stirring the sample.

10. A method of determining liquid absorption of an aggregate, the method comprising:
    providing a sample of the aggregate;
    adding liquid to the sample;
    subjecting the sample to a light source signal;
    monitoring a light reflected signal reflected from the sample; and
    controlling one of addition of liquid to the sample and removal of liquid from the sample as a function of the light reflected signal;
    wherein the controlling step comprises controlling addition of liquid to the sample;
    wherein liquid is added to the sample only until the reflected light signal reaches a predetermined value indicative of the sample being at a saturated surface dry state.

11. The method of claim 10 wherein the predetermined value of the reflected light signal is determined by averaging the reflected light signal reflected from the dry sample with the reflected light signal reflected from the sample wetter than a saturated surface dry state.

12. The method of claim 11 wherein the reflected light signal reflected from the dry sample is measured and the reflected light signal reflected from the sample wetter than the saturated surface dry state is approximately a constant voltage.

13. The method of claim 10 wherein the sample is weighed in a dry state and at the saturated surface dry state to determine a percentage by weight of the liquid absorbed into the aggregate and hence a percentage by weight of absorption of a binder into the aggregate.

14. A method of determining liquid absorption of an aggregate, the method comprising:
    providing a sample of the aggregate;
    adding liquid to the sample;
    subjecting the sample to a light source signal;
    monitoring a light reflected signal reflected from the sample; and
    controlling one of addition of liquid to the sample and removal of liquid from the sample as a function of the light reflected signal;
    wherein the controlling step comprises controlling removal of liquid from the sample by controlling heating of the sample.

15. Apparatus for determining liquid absorption of an aggregate, said apparatus comprising:
    a support for supporting a sample of the aggregate;
    a liquid source for adding liquid to the sample;
    a light source which subjects the sample to a light source signal;
    a light sensor which senses a reflected light signal reflected from the sample; and
    a processor/controller which controls one of addition of liquid from said liquid source to the sample and removal of liquid from the sample as a function of the reflected light signal.

16. The apparatus of claim 15 wherein said processor/controller controls addition of liquid from said liquid source to the sample.

17. The apparatus of claim 16 wherein said liquid source is a water source.

18. The apparatus of claim 16 wherein said light source is an infrared source.

19. The apparatus of claim 16 wherein said light sensor is an infrared detector.

20. The apparatus of claim 16 further including an agitator for agitating the sample.

21. The apparatus of claim 20 wherein said agitator is a turntable which moves the sample in an orbital motion.

22. The apparatus of claim 20 wherein said agitator is a turntable which moves the sample in a wobbling motion.

23. The apparatus of claim 20 wherein said agitator is a stirrer which stirs the sample.

24. The apparatus of claim 20 wherein said agitator is a turntable which moves the sample in an orbital motion and in a wobbling motion and a stirrer which stirs the sample.

25. The apparatus of claim 16 wherein said support is a bowl which contains the sample.

26. Apparatus for determining liquid absorption of an aggregate, said apparatus comprising:
   a support for supporting a sample of the aggregate;
   a liquid source for adding liquid to the sample;
   a light source which subjects the sample to a light source signal;
   a light sensor which senses a reflected light signal reflected from the sample; and
   a processor/controller which controls one of addition of liquid from said liquid source to the sample and removal of liquid from the sample as a function of the reflected light signal;
   wherein said processor/controller controls addition of liquid from said liquid source to the sample;
   wherein said support is a bowl which contains the sample;
   wherein the bowl includes an island in a center thereof to direct the sample radially outwardly.

27. The apparatus of claim 25 wherein said bowl includes a lid thereon.

28. Apparatus for determining liquid absorption of an aggregate, said apparatus comprising:
   a support for supporting a sample of the aggregate;
   a liquid source for adding liquid to the sample;
   a light source which subjects the sample to a light source signal;
   a light sensor which senses a reflected light signal reflected from the sample; and
   a processor/controller which controls one of addition of liquid from said liquid source to the sample and removal of liquid from the sample as a function of the reflected light signal;
   wherein said processor/controller controls addition of liquid from said liquid source to the sample;
   wherein said support is a bowl which contains the sample;
   wherein said bowl includes a lid thereon;
   wherein said lid includes a dome offset from a center of said lid, and wherein said light source and light sensor are positioned such that the light source signal and the light reflected signal pass through said dome normal to a surface of said dome.

29. The apparatus of claim 28 wherein said light source is an infrared source and said light sensor is an infrared detector.

30. The apparatus of claim 16 further including a cabinet containing said support, liquid source, light source and light sensor.

31. The apparatus of claim 30 wherein said cabinet includes a door providing access to an interior thereof.

32. The apparatus of claim 31 further including a bracket mounted to an underside of said door, said light source and light sensor mounted to said bracket.

33. Apparatus for determining liquid absorption of an aggregate, said apparatus comprising:
   a support for supporting a sample of the aggregate;
   a liquid source for adding liquid to the sample;
   a light source which subjects the sample to a light source signal;
   a light sensor which senses a reflected light signal reflected from the sample; and
   a processor/controller which controls one of addition of liquid from said liquid source to the sample and removal of liquid from the sample as a function of the reflected light signal;
   wherein said processor/controller controls addition of liquid from said liquid source to the sample;
   wherein said processor/controller processes the reflected light signal as a function of time and controls addition of liquid to the sample such that liquid is added to the sample only until the reflected light signal reaches a predetermined value indicative of the sample being at a saturated surface dry state.

34. The apparatus of claim 33 wherein the predetermined value of the reflected light signal is determined by averaging the reflected light signal reflected from the dry sample with the reflected light signal reflected from the sample wetter than a saturated surface dry state.

35. The apparatus of claim 34 wherein the reflected light signal reflected from the dry sample is measured and the reflected light signal reflected from the sample wetter than the saturated surface dry state is approximately a constant voltage.

36. The apparatus of claim 33 further including a weight indicating device for weighing the sample in a dry state and in the saturated surface dry state, said apparatus thereby being additionally able to determine a percentage by weight of the liquid absorbed into the aggregate and hence a percentage by weight of absorption of a binder into the aggregate.

37. Apparatus for determining liquid absorption of an aggregate said apparatus comprising:
   a support for supporting a sample of the aggregate;
   a liquid source for adding liquid to the sample;
   a light source which subjects the sample to a light source signal;
   a light sensor which senses a reflected light signal reflected from the sample; and
   a processor/controller which controls one of addition of liquid from said liquid source to the sample and removal of liquid from the sample as a function of the reflected light signal;
   further including a heater for heating the sample, said processor/controller controlling removal of liquid from the sample by controlling said heater.

38. Apparatus for determining a saturated, surface-dry state of aggregate, said apparatus comprising:
   a cabinet;
   a bowl for containing a sample of the aggregate;
   a water source in fluid communication with said bowl for adding water to the sample;
   an infrared source for subjecting the sample to an infrared source signal;
   an infrared detector for detecting an infrared reflected signal reflected from the sample; and
   a processor/controller which processes the reflected infrared signal as a function of time and controls addition of water to the sample such that water is added to the sample only until the infrared reflected signal reaches a predetermined value indicative of the sample being at a saturated surface dry state.

39. The apparatus of claim 38 wherein the predetermined value of the infrared reflected signal is determined by averaging the infrared reflected signal reflected from the dry sample with the infrared reflected signal reflected from the sample wetter than a saturated surface dry state.

40. The apparatus of claim 39 wherein the infrared reflected signal reflected from the dry sample is measured and the infrared reflected signal reflected from the sample wetter than the saturated surface dry state is approximately a constant voltage.

41. The apparatus of claim 38 further comprising a pump which pumps water from said water source into said bowl, said processor/controller controlling said pump.

42. The apparatus of claim 38 further including a turntable movably mounted in said cabinet, said bowl supported on said turntable.

43. The apparatus of claim 42 wherein said turntable is mounted for orbital motion.

44. The apparatus of claim 42 wherein said turntable is mounted for wobbling motion.

45. The apparatus of claim 38 wherein said bowl includes a stirrer for stirring the sample.

46. The apparatus of claim 42 wherein said turntable is mounted for orbital and wobbling motion and wherein said bowl includes a stirrer for stirring the sample.

47. The apparatus of claim 38 wherein said bowl includes a lid thereon and wherein said lid includes a dome offset from a center of said lid, and wherein said infrared source and infrared detector are positioned such that the infrared source signal and the infrared reflected signal pass through said dome normal to a surface of said dome.

48. The apparatus of claim 38 further including a weight indicating device for weighing the sample in a dry state and in the saturated surface dry state, said apparatus thereby being additionally able to determine a percentage by weight of the water absorbed into the aggregate and hence a percentage by weight of absorption of a binder into the aggregate.

49. Apparatus for determining a percentage by weight of water absorbed into an aggregate and hence a percentage by weight of absorption of a binder into the aggregate, said apparatus comprising:
   a cabinet;
   a bowl for containing a sample of the aggregate;
   a pump in said cabinet for pumping water from a water source into said bowl;
   an infrared source for subjecting the sample to an infrared source signal;
   an infrared detector for detecting an infrared reflected signal reflected from the sample;
   a processor/controller which processes the reflected infrared signal as a function of time and controls addition of water to the sample by controlling said pump such that water is added to the sample only until the infrared reflected signal reaches a predetermined value indicative of the sample being at a saturated surface dry state; and
   a weight indicating device for measuring the weight of the sample.

50. The apparatus of claim 49 wherein the predetermined value of the infrared reflected signal is determined by averaging the infrared reflected signal reflected from the dry sample with the infrared reflected signal reflected from the sample wetter than a saturated surface dry state.

51. The apparatus of claim 50 wherein the infrared reflected signal reflected from the dry sample is measured and the infrared reflected signal reflected from the sample wetter than the saturated surface dry state is approximately a constant voltage.

52. The apparatus of claim 49 further comprising an agitator in said cabinet for agitating said bowl and hence the sample.

53. The apparatus of claim 52 wherein said agitator is a turntable movably mounted in said cabinet, said bowl supported on said turntable.

54. The apparatus of claim 53 wherein said turntable is mounted for orbital motion.

55. The apparatus of claim 53 wherein said turntable is mounted for wobbling motion.

56. The apparatus of claim 53 wherein said turntable is mounted for orbital and wobbling motion.

57. The apparatus of claim 52 wherein said agitator is a stirrer for stirring the sample.

58. The apparatus of claim 52 wherein said agitator is a turntable, upon which said bowl is supported, mounted for orbital and wobbling motion and a stirrer for stirring the sample.

59. The apparatus of claim 49 wherein said bowl includes a lid thereon and wherein said lid includes a dome offset from a center of said lid, and wherein said infrared source and infrared detector are positioned such that the infrared source and the infrared reflected signals pass through said dome normal to a surface of said dome.

60. Apparatus for determining liquid absorption of an aggregate, said apparatus comprising:
   a support for supporting a sample of the aggregate;
   a liquid source for adding liquid to the sample;
   a light source which subjects the sample to a light source signal;
   a light sensor which senses a reflected light signal reflected from the sample;
   a processor/controller which controls one of addition of liquid from said liquid source to the sample and removal of liquid from the sample as a function of the reflected light signal; and
   a weight indicating device for measuring the weight of the sample.

61. Apparatus for determining liquid absorption of an aggregate, said apparatus comprising:
   a support for supporting a sample of the aggregate;
   a liquid source for adding liquid to the sample;
   a light source which subjects the sample to a light source signal;
   a light sensor which senses a reflected light signal reflected from the sample;
   a processor/controller which processes the reflected light signal as a function of time and controls addition of water to the sample such that water is added to the sample only until the reflected light signal reaches a predetermined value indicative of the sample being at a saturated surface dry state; and
   a weight indicating device for measuring the weight of the sample.

62. Apparatus for determining a saturated, surface-dry satus of an aggregate, said apparatus comprising:
   a cabinet;
   a bowl for containing a sample of the aggregate;
   a water source in fluid communication with said bowl for adding water to the sample;

an infrared source for subjecting the sample to an infrared source signal;

an infrared detector for detecting an infrared reflected signal reflected from the sample;

a processor/controller which processes the reflected infrared signal as a function of time and controls addition of water to the sample such that water is added to the sample only until the infrared reflected signal reaches a predetermined value indicative of the sample being at a saturated surface dry state; and a weight indicating device for measuring the weight of the sample.

63. Apparatus for determining liquid absorption of an aggregate, said apparatus comprising:

a support for supporting a sample of the aggregate;

a liquid source for adding liquid to the sample;

a light source which subjects the sample to a light source signal;

a light sensor which senses a reflected light signal reflected from the sample;

a processor/controller which controls one of addition of liquid from said liquid source to the sample and removal of liquid from the sample as a function of the reflected light signal;

further including a heater for heating the sample, said processor/controller controlling removal of liquid from the sample by controlling said heater; and a weight indicating device for measuring the weight of the sample.

64. Apparatus for determining liquid absorption of an aggregate, said apparatus comprising:

a support for supporting a sample of the aggregate;

a liquid source for adding liquid to the sample;

an infrared source which subjects the sample to an infrared source signal;

an infrared detector which detects an infrared reflected signal reflected from the sample; and a processor/controller which controls one of addition of liquid from said liquid source to the sample and removal of liquid from the sample as a function of the infrared reflected signal;

further including a heater for heating the sample, said processor/controller controlling removal of liquid from the sample by controlling said heater; and a weight indicating device for measuring the weight of the sample.

65. Apparatus for determining liquid absorption of an aggregate, said apparatus comprising:

a support for supporting a sample of the aggregate;

a liquid source for adding liquid to the sample;

an infrared source which subjects the sample to an infrared source signal;

an infrared detector which detects an infrared reflected signal reflected from the sample;

a processor/controller which controls one of addition of liquid from said liquid source to the sample and removal of liquid from the sample as a function of the infrared reflected signal;

further including a heater for heating the sample, said processor/controller controlling removal of liquid from the sample by controlling said heater; and said infrared source also functioning as said heater for heating the sample, said processor/controller controlling removal of liquid from the sample by controlling said infrared source.

* * * * *

UNITED STATES PATENT AND TRADEMARK OFFICE
CERTIFICATE OF CORRECTION

PATENT NO. : 6,486,475 B1
DATED : November 26, 2002
INVENTOR(S) : Earle, Sr. et al.

It is certified that error appears in the above-identified patent and that said Letters Patent is hereby corrected as shown below:

Column 6,
Line 53, reads "aggregate. $V_{ssd}$ can" and should read -- aggregate, $V_{ssd}$ can --.

Column 7,
Line 21, reads "condition. the" and should read -- condition, the --.

Column 10,
Line 38, reads "an aggregate said apparatus" and should read -- an aggregate, said apparatus --.

Signed and Sealed this

Fifteenth Day of July, 2003

JAMES E. ROGAN
*Director of the United States Patent and Trademark Office*